US012734162B2

(12) United States Patent
Pontisso et al.

(10) Patent No.: US 12,734,162 B2
(45) **Date of Patent: *Sep. 15, 2026**

(54) SERPINB3 INHIBITOR PIPERIDINPROPIONIC ACID FOR TUMOR TREATMENT

(71) Applicant: UNIVERSITA' DEGLI STUDI DI PADOVA, Padua (IT)

(72) Inventors: Patrizia Pontisso, Padua (IT); Alessandra Biasiolo, Selvazzano Dentro (IT); Andrea Martini, Padua (IT); Santina Quarta, Villaguattera di Rubano (IT); Mariagrazia Ruvoletto, Vigonovo (IT); Cristian Turato, Villafranca Padovana (IT); Gianmarco Villano, Padua (IT)

(73) Assignee: UNIVERSITA' DEGLI STUDI DI PADOVA, Padua (IT)

( * ) Notice: Subject to any disclaimer, the term of this patent is extended or adjusted under 35 U.S.C. 154(b) by 945 days.

This patent is subject to a terminal disclaimer.

(21) Appl. No.: 17/629,791

(22) PCT Filed: Jul. 23, 2020

(86) PCT No.: PCT/EP2020/070785

§ 371 (c)(1),
(2) Date: Jan. 25, 2022

(87) PCT Pub. No.: WO2021/013921

PCT Pub. Date: Jan. 28, 2021

(65) Prior Publication Data

US 2022/0265626 A1 Aug. 25, 2022

(30) Foreign Application Priority Data

Jul. 25, 2019 (IT) ........................ 102019000012930

(51) Int. Cl.
*A61K 31/4453* (2006.01)
*A61P 35/00* (2006.01)

(52) U.S. Cl.
CPC .......... *A61K 31/4453* (2013.01); *A61P 35/00* (2018.01)

(58) Field of Classification Search
CPC ............................ A61K 31/4453; A61P 35/00
See application file for complete search history.

(56) References Cited

U.S. PATENT DOCUMENTS

2012/0283302 A1* 11/2012 Kaneko .................. A61P 37/08 514/390

FOREIGN PATENT DOCUMENTS

| JP | 2009242345 A | 10/2009 |
|---|---|---|
| WO | 2018163119 A1 | 9/2018 |

OTHER PUBLICATIONS

Turato C, Fornari F, Pollutri D, Fassan M, Quarta S, Villano G, Ruvoletto M, Bolondi L, Gramantieri L, Pontisso P. MIR-122 Targets SerpinB3 and Is Involved in Sorafenib Resistance in Hepatocellular Carcinoma. J Clin Med. Feb. 1, 2019;8(2):171. doi: 10.3390/jcm8020171. PMID: 30717317; PMCID: PMC6406326. (Year: 2019).*

Verhoeckx K, Cotter P, López-Expósito I, Kleiveland C, Lea T, Mackie A, Requena T, Swiatecka D, Wichers H, editors. The Impact of Food Bioactives on Health: in vitro and ex vivo models [Internet]. Cham (CH): Springer; 2015. PMID: 29787039. (Year: 2015).*

Leukemia and Lymphoma Society. Myelofibrosis Facts, Nov. 2015, www.lls.org/sites/default/files/file_assets/FS14_Myelofibrosis_Fact%20Sheet_Final9.12.pdf. (Year: 2015).*

Cholankeril G, Patel R, Khurana S, Satapathy SK. Hepatocellular carcinoma in non-alcoholic steatohepatitis: Current knowledge and implications for management. World J Hepatol. Apr. 18, 2017;9(11):533-543. doi: 10.4254/wjh.v9.i11.533. PMID: 28469809; PMCID: PMC5395802. (Year: 2017).*

S. Costantini, G. Di Bernardo, M. Cammarota, G. Castello, G. Colonna, Gene expression signature of human HepG2 cell line, Gene, vol. 518, Issue 2, 2013, pp. 335-345, ISSN 0378-1119, https://doi.org/10.1016/j.gene.2012.12.106. (Year: 2013).*

Turato C, Pontisso P. SERPINB3 (serpin peptidase inhibitor, clade B (ovalbumin), member 3). Atlas Genet Cytogenet Oncol Haematol. 2015;19(3):202-209. doi: 10.4267/2042/56413. PMID: 25984243; PMCID: PMC4430857. (Year: 2015).*

Andres AL, Gong X, Di K, Bota DA. Low-doses of cisplatin injure hippocampal synapses: a mechanism for 'chemo' brain? Exp Neurol. May 2014;255:137-44. doi: 10.1016/j.expneurol.2014.02.020. Epub Mar. 2, 2014. PMID: 24594220; PMCID: PMC4059602. (Year: 2014).*

Arzumanian VA, Kiseleva OI, Poverennaya EV. The Curious Case of the HepG2 Cell Line: 40 Years of Expertise. Int J Mol Sci. Dec. 4, 2021;22(23):13135. doi: 10.3390/ijms222313135. PMID: 34884942; PMCID: PMC8658661. (Year: 2021).*

Search Report and Written Opinion of PCT/EP2020/070785 of Nov. 16, 2020.

* cited by examiner

*Primary Examiner* — Fereydoun G Sajjadi
*Assistant Examiner* — Anna Grace Kuckla
(74) *Attorney, Agent, or Firm* — Silvia Salvadori, P.C.; Silvia Salvadori

(57) ABSTRACT

The invention concerns the use of 1-Piperidinpropionic acid or salts thereof, for the treatment of tumors that express SerpinB3.

5 Claims, 7 Drawing Sheets

Specification includes a Sequence Listing.

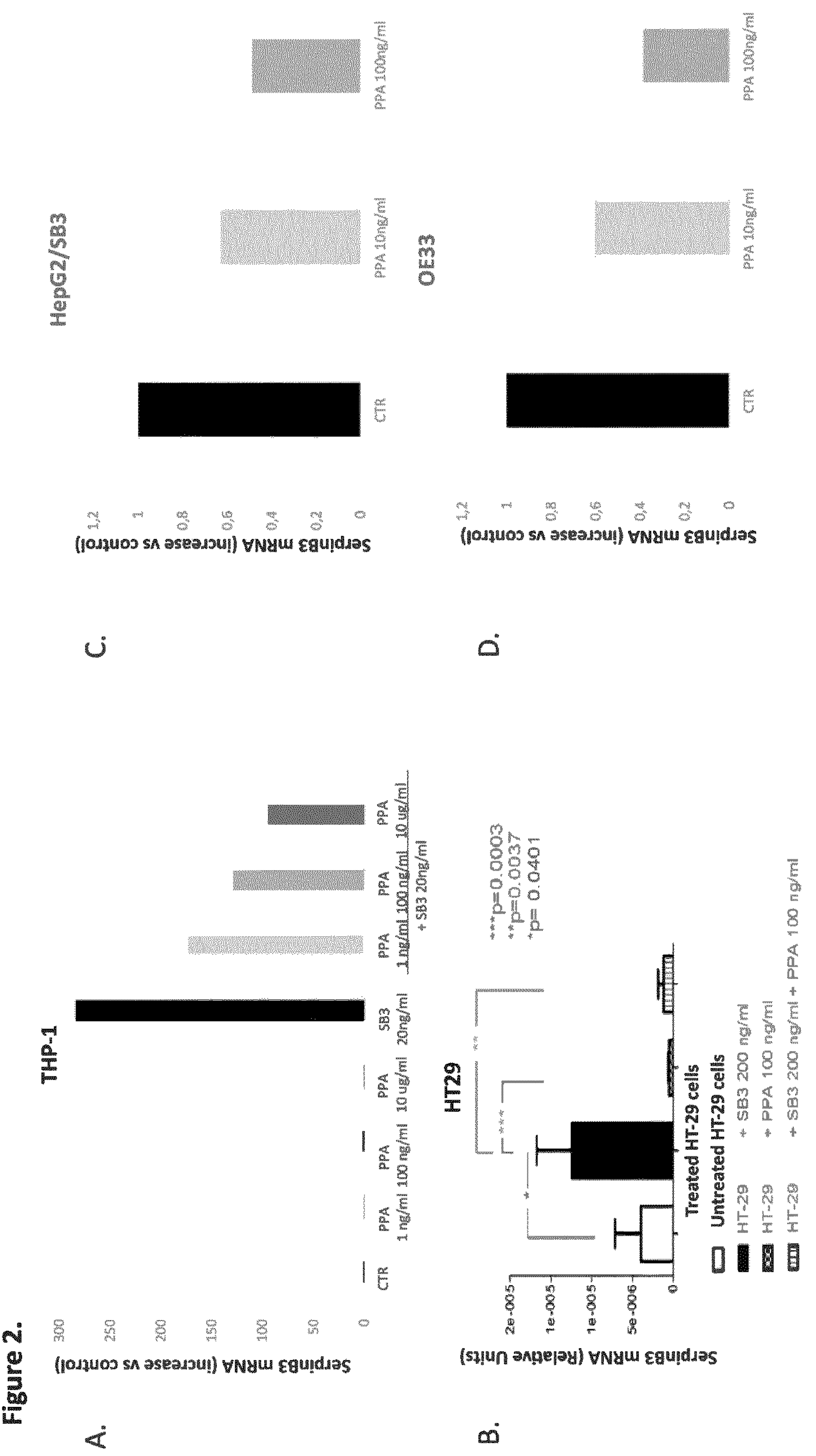
Figure 2.
A.
THP-1
SerpinB3 mRNA (increase vs control)
300
250
200
150
100
50
0
CTR
PPA 1 ng/ml
PPA 100 ng/ml
PPA 10 ug/ml
SB3 20ng/ml
PPA 1 ng/ml
PPA 100 ng/ml
PPA 10 ug/ml
+ SB3 20ng/ml
B.
HT29
SerpinB3 mRNA (Relative Units)
2e-005
1e-005
1e-005
5e-006
0
***p=0.0003
**p=0.0037
*p= 0.0401
Treated HT-29 cells
Untreated HT-29 cells
HT-29
HT-29 + SB3 200 ng/ml
HT-29 + PPA 100 ng/ml
HT-29 + SB3 200 ng/ml + PPA 100 ng/ml
C.
HepG2/SB3
SerpinB3 mRNA (increase vs control)
1,2
1
0,8
0,6
0,4
0,2
0
CTR
PPA 10ng/ml
PPA 100ng/ml
D.
OE33
SerpinB3 mRNA (increase vs control)
1,2
1
0,8
0,6
0,4
0,2
0
CTR
PPA 10ng/ml
PPA 100ng/ml

A.

B.

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: PCR sense primer

<400> SEQUENCE: 1
aactcctggg tggaaagtca a 21

<210> SEQ ID NO 2
<211> LENGTH: 22
<212> TYPE: DNA
<213> ORGANISM: Artificial Sequence
<220> FEATURE:
<223> OTHER INFORMATION: PCR reverse primer

<400> SEQUENCE: 2
accaatgtgg tattgctgcc aa 22

SERPINB3 INHIBITOR PIPERIDINPROPIONIC ACID FOR TUMOR TREATMENT

Sequence listing ASCII file Sequence.txt, created on Jan. 24, 2022 and of size 590 bytes is incorporated herein by reference.

This application is a U.S. national stage of PCT/EP2020/070785 filed on 23 Jul. 2020, which claims priority to and the benefit of Italian Patent Application No. 102019000012930 filed on 25 Jul. 2019, the contents of which are incorporated herein by reference in their entireties.

FIELD OF THE INVENTION

The invention concerns the use of 1-Piperidinpropionic acid or salts thereof, for the treatment of tumors that express SerpinB3.

STATE OF THE ART

SerpinB3 is a member of the serine-protease inhibitor family (Serpins), physiologically expressed in squamous epithelia (Kato et al., Anticancer Res. 1996; 199616(4B): 2149-2153). Said serpin is also expressed in endodermal and ectodermal tumors (Turato et al, Atlas Genet Cytogenet Oncol Haematol. 2015; 19:202-209), where it causes resistance to anti-neoplastic drugs. Its carcinogenic effect is due to its following properties:

a) it has an anti-apoptotic effect and protects cells from the toxicity of chemotherapeutic drugs with a pro-oxidant action through its binding to complex I of the respiratory chain (Ciscato et al, Oncotarget 2014, 5: 2418-2427);

b) it induces epithelial-mesenchymal transition and decrease of desmosomal junctions, causing cell proliferation, increase in the number of colonies in soft agar and cell invasiveness (Quarta et al. J Pathol 2010; 221: 343-356);

c) it induces over-expression of pro-oncogene molecules such as Myc, β-catenin and TGFβ (Turato et al. Br J Cancer 2014; 110: 2708-2715, Turato et al. Sci Rep 2015; 5: 17701); d) it induces the synthesis of proinflammatory cytokines, such as IL-6 and TNF-α (Catanzaro et al, Nat. Commun. 2014:5, 3729), in addition to inhibiting the intratumoral infiltration of natural killer cells (Suminami et al. Cancer Res 2001; 61:176-180) and reducing immunosurveillance through the induction of PD-L1 and reduction of immune activation markers, such as CD80, CD86, TLR4, and CD38 (Turato et al. Cancer Sci 2019; 110:1552-1563);

e) it is a target of miR-122 with antineoplastic activity in the liver and is associated with a tumor stem profile (Turato et al. J Clin. Med 2019 Feb. 1; 8(2). pii: E171).

In light of said premises, the presence of SerpinB3 in the most aggressive tumor forms which are less responsive to antineoplastic drugs is understandable. SerpinB3 is in fact expressed in primitive liver tumors with an unfavourable prognosis (Turato et al. Br J Cancer 2014; 110: 2708-2715), in colon and pancreatic tumors in the most advanced stage (Catanzaro et al, Nat. Commun. 2014:5, 3729), in lung, esophagus, breast and ovary tumors with poor response to chemotherapy (Ciscato et al, Oncotarget 2014, 5: 2418-2427; Turato et al Cancer Sci 2019; 110:1552-1563).

At present, compounds that are effective at reducing the expression of SerpinB3 in said tumor forms are not described in the literature.

The aim of the present invention is therefore to provide new compounds for the treatment of tumors that express SerpinB3 (or SCCA-1, squamous cell carcinoma antigen-1), based on the inhibition of the production of SerpinB3.

SUMMARY OF THE INVENTION

The invention therefore concerns the use of 1-Piperidinpropionic acid or salts thereof, for the treatment of chemoresistant tumors that express SerpinB3. The dependent claims describe particular embodiments of the invention in which it has surprisingly been found that 1-Piperidin-Propionic Acid (PPA) is able to reduce the synthesis of SerpinB3 in tumor cells that express high levels of said molecule and the cell proliferation induced by it, it reduces the expression of genes that cause resistance to chemotherapeutic drugs, it improves the efficacy of antineoplastic drugs in tumor cells that express SerpinB3 and it significantly reduces the synthesis of inflammatory cytokines involved in the typical immune deficiency of the tumor.

DESCRIPTION OF THE DRAWINGS

The invention will now be described in detail and with reference to the accompanying FIGS. 1-7.

FIG. 2. Experiments of PPA-induced inhibition of exogenous SerpinB3 on THP1 cells (FIG. 2A), on HT29 cells (FIG. 2B) and of endogenous constitutive SerpinB3 on HepG2/SB3 cells (FIG. 2C and on OE33 cells (FIG. 2D). As described in Example 2, a marked increase in SerpinB3 mRNA can be seen through the treatment with exogenous SerpinB3 (SB3) (in particular in THP-1 cells); the addition of PPA reduces both its constitutive expression and the one induced by exogenous treatment. Concentrations of 1-10 ng/ml are already able to reduce the synthesis of SerpinB3 by about 50%.

Figure 1:
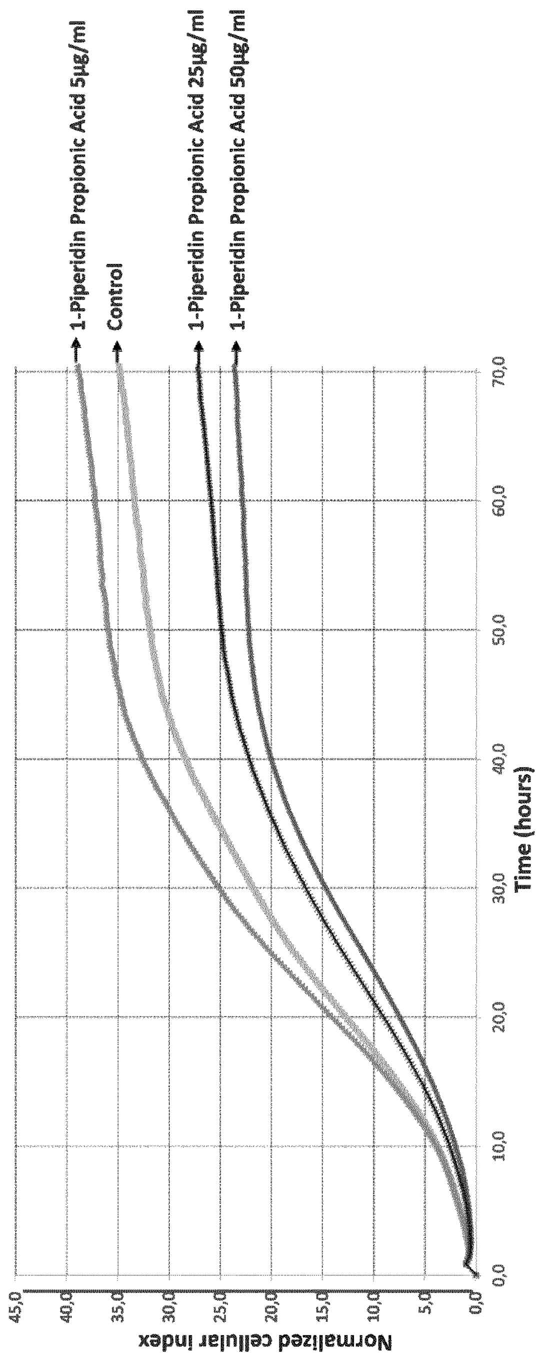
FIG. 1. Cell proliferation curve on HepG2 liver tumor derived cells using different concentrations of 1-Piperidin-Propionic Acid (PPA). As described in Example 1, it should be noted that this concentration is markedly higher than the biologically active PPA concentrations, whose normal range of use was 10-100 ng/ml.

*p=<0.01 SerpinB3/KO vs SerpinB3/TG and vs controls for panels A and B and for control mice treated with PPA vs untreated for panel C.

DETAILED DESCRIPTION OF THE INVENTION

Despite the progress achieved in the oncology field and the availability of more and more effective antitumor drugs, there are still forms of tumor that are not sensitive to the chemotherapy effect and are typically those with the most unfavourable prognosis.

Given that the SerpinB3 molecule plays an important role in the determinism of the resistance to chemotherapeutic drugs and in reducing tumor immunosurveillance, the present invention has proposed to identify an inhibitor of the production of SerpinB3, as a drug to counteract the resistance to chemotherapy and restore the surveillance of the immune system in solid tumors overexpressing SerpinB3.

The 1-piperidinpropionic acid in the prior art is used on a cosmetic level for topical anti-ageing treatments and has never been proposed for the treatment of chemoresistant tumors overexpressing SerpinB3.

In the present invention when the following definitions are used:

"1-piperidinpropionic acid" or "PPA" is referred to the compound of formula:

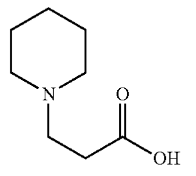 [SMILES: O=C(O)CCN1CCCCC1]

having the molecular formula: $C_8H_{15}NO_2$ and name IUPAC 3-(1-piperidinyl)propanoic acid;

with "salts of 1-piperidinpropionic acid" it is intended to include a hydrochloride, a sulphate, a phosphate, a hydrobromide, a sodium salt, a potassium salt, a magnesium salt, a calcium salt, an ammonium salt, an acetate, a lactate, a maleate, a fumarate, a tartrate, a citrate, a methanesulfonate, a p-tolylsulfonyloxy, a triethanolamine, a diethanolamine and salts of amino acids.

In fact, the invention concerns the use of 1-Piperidinpropionic acid or salts thereof, for the treatment of tumors that express SerpinB3.

Since to date a significant proportion of tumors are resistant to available therapies, the 1-piperidin propionic acid is proposed as a new treatment for said forms.

Advantageously, the PPA: a) is easily available on the market, b) was well tolerated in the experimental model, c) does not degrade easily, d) has a low cost.

The experiments carried out in our laboratories and shown in the examples have demonstrated that PPA, up to the concentration of 5 μg/ml, does not produce toxicity in cells derived from liver tumor HepG2 (HB8065), incubated with increasing concentrations of PPA (Example 1).

In a preferred embodiment, in the use of 1-Piperidinpropionic acid or salts thereof according to the present invention, said tumor is a solid tumor, and said solid tumor is a liver, colon, pancreas, lung, esophagus, breast, prostate, ovary tumor or a lymphoma.

In a further preferred embodiment, in the use of 1-Piperidinpropionic acid or salts thereof according to the present invention, said tumor is a tumor of the hematopoietic tissues, preferably a leukemia.

In a further embodiment, said solid tumor is a primary or secondary tumor and the cells of said solid tumor overexpress SerpinB3.

From the point of view of the gene expression, the ability of PPA to inhibit the expression of SerpinB3 both induced by adding exogenous SerpinB3 using both the monocytic THP-1 line that does not express SerpinB3 and the cell line derived from HT29 colon tumor expressing low levels of SerpinB3 has been evaluated. PPA was added to the cultured cells at a concentration of 1-100 ng/ml alone or in combination with recombinant SerpinB3 at a concentration of 20-200 ng/ml. For the inhibition of the expression of endogenous SerpinB3, tumor cells expressing constitutively SerpinB3 deriving from oesophagus (OE33) and liver tumor cells HepG2 transfected to stably express SerpinB3 (HepG2/SB3) and that in previous experiments had demonstrated significantly higher proliferative activity and cell invasiveness than the SerpinB3 non-expressing esophagus lines or HepG2 transfected with only the empty plasmid were used. The expression of SerpinB3 was found to be markedly increased by the treatment with exogenous SerpinB3 (in particular in THP-1 cells) and the addition of PPA reduces in a dose-dependent manner both its expression induced by the exogenous treatment and its constitutive one. It should be noted that concentrations of 1-10 ng/ml are already able to reduce the synthesis of SerpinB3 by about 50% (Example 2).

According to another aspect, in the present invention, the use of 1-Piperidinpropionic acid or salts thereof is for the treatment of solid tumors that express SerpinB3, wherein the solid tumor is a chemoresistant tumor.

The use of the PPA in the oncological field is proposed as an adjuvant in the treatment of chemoresistant tumors overexpressing SerpinB3.

One of the main causes of the antitumor treatment failure is the development of resistance to the effects of drugs by the cells.

This is because the cells that make up a tumor mass are not all the same. One of the characteristics of cancer is the so-called genetic instability: DNA mutations occur with an uncommon rapidity and cause tumor cells to never be genetically identical. When the mass is exposed to the action of an antitumor drug, the cells sensitive to its effects die, but some of them, including tumor stem cells, have by themselves or have acquired different genetic characteristics over time and are therefore able to resist the therapy. The latter will continue to multiply and causes the whole tumor to become resistant to the treatment in a short time. It should be noted that SerpinB3 is associated with a stem tumor profile (Turato et al. J Clin. Med 2019 Feb. 1; 8(2). pii: E171).

The use of PPA in the treatment of solid tumors as described in the present invention has surprisingly proved to be effective precisely for tumors that are resistant to drugs and whose resistance is reverted precisely through the use of PPA.

To evaluate possible changes in cell proliferation induced by PPA, the THP-1 cell line of monocytic origin, incubated with exogenous SerpinB3 (20 ng/ml), which in previous experiments had induced not only a marked increase in the synthesis of endogenous SerpinB3, but also a corresponding increase in cell proliferation was used. The addition of PPA was not only able to reduce the expression of SerpinB3, but a contextual reduction in proliferative activity which was proved to be dose-dependent was also documented (Example 3).

In a preferred embodiment, in the use according to the present invention said chemoresistant tumor is resistant to one or more chemotherapeutic drugs, and said chemotherapeutic drug is chosen from the group consisting of cisplatin, sorafenib, 5-fluorouracil or methotrexate.

In yet another aspect, the use of 1-Piperidinpropionic acid or salts thereof, according to the present invention, is for the treatment of solid tumors that express SerpinB3, wherein the solid tumor is a chemoresistant tumor and wherein the chemoresistance is reverted.

In an even more preferred embodiment, wherein in these solid SerpinB3 overexpressing tumors the surveillance of the immune system is restored.

Surprisingly, it has been seen that SerpinB3, in addition to inducing resistance to cell death and increased proliferation, is able to induce a reduction in tumor immunosurveillance, in particular through the increased production of cytokines such as CCL15, recently involved in the reduction of immune surveillance in hepatocellular carcinoma, and the immune checkpoint molecule PD-L1, towards which several new antitumor drugs are directed. The THP-1 monocytic cells, after stimulation with exogenous SerpinB3, which may be present in the tumor microenvironment, produce high levels of cytokines, especially CCL15 and PD-L1 and these are markedly reduced by the PPA even at very low doses (1 ng/ml). These data document how PPA is able to restore immune control through the suppression of immune depression induced by SerpinB3 (Example 4).

The SerpinB3 molecule is known to induce resistance to chemotherapy treatment. In order to evaluate whether the inhibition of said molecule is able to increase the therapeutic efficacy of antitumor drugs, HepG2 cells stably transfected to overexpress SerpinB3 (HepG2/SB3) and HepG2 cells transfected with only the empty plasmid (HepG2/CTR) have been incubated with several antitumor drugs in the absence or presence of PPA. The results obtained confirmed that the presence of SerpinB3 confers greater resistance to cell death induced by Cisplatin and Sorafenib, while the sensitivity to 5-Fluorouracil and Methotrexate was not different in the two cell lines. The addition of PPA resulted in a significant reduction of viability in cells with high levels of SerpinB3, treated with Cisplatin, Sorafenib and 5-Fluorouracil, while it did not change in the treatment with Methotrexate (Example 5). In order to understand more fully whether the resistance to chemotherapeutic drugs induced by SerpinB3 is exclusively linked to the increased resistance to cell death following the reduced activation of the mitochondrial proapoptotic cascade, the genes involved in multiple resistance to chemotherapeutic drugs have been analysed. It has been documented that the presence of SerpinB3 causes an increase in two genes involved in the resistance to chemotherapeutic drugs, in particular MDR1 and MRD2 and the treatment with PPA causes a reduction of their expression in a dose-dependent manner. These results support the hypothesis that also the induction of MDR genes contributes to the drug resistance caused by SerpinB3, the expression of which genes is markedly reduced by PPA (Example 6). In a further aspect, the present invention relates to a method for treating a tumor patient, in which said tumor is chemoresistant, said method comprising the step of administering a therapeutically effective amount of 1-Piperidinpropionic acid or salts thereof.

In the method according to the present invention, said chemoresistance is reverted. In conclusion, the experiments carried out demonstrate:

1) PPA does not induce cellular toxicity at pharmacologically active concentrations, capable of inhibiting the synthesis of SerpinB3 at the cellular level.
2) PPA is able to inhibit the expression of SerpinB3 both induced by exogenous SerpinB3 and its endogenous constitutive expression
3) PPA is able to reduce SerpinB3-induced cell proliferation
4) PPA at very low doses (1 ng/ml) is able to inhibit the expression of cytokines which reduce immunosurveillance and which are induced by SerpinB3
5) PPA is able to restore sensitivity to chemotherapeutic drugs and this effect, at least in part, is linked to the reduction of MDR drug resistance genes induced by SerpinB3.

The following examples of embodiments of the present invention are given below by way of illustration.

EXAMPLES

Example 1. PPA Does Not Induce Cellular Toxicity at Biologically Active Concentrations HepG2 liver tumor derived cells (HB8065), incubated with increasing concentrations of 1'-Piperidin propionic acid (PPA) in a range of 5-50 μg/ml were used and real-time cell proliferation was analysed, using xCELLigence instrument (ACEA Biosciences, Inc., San Diego, CA, USA), according to the supplier's instructions. In each well of an E-16 plate, $4\times10^4$ HepG2 cells (HB8065) were seeded in quadruplicate, cultured in complete MEM medium (Sigma-Aldrich, Milan, Italy) supplemented with 10% fetal calf serum (Sigma-Aldrich, Milan, Italy), 100 U/mL of penicillin, 100 μg/ml of streptomycin, and 20 mM L-glutamine (Sigma-Aldrich, Milan, Italy) and 1% of MEM Non Essential Amino Acids. The cells were kept in an incubator at 37° C. with 95% humidity and 5% $CO_2$ saturation. The complete medium was used as a control. The RTCA system monitored the electrical impedance, which is directly proportional to the number of cells present per well, indicated as Cell Index every 5 min for over 60 hours. The cell proliferation curves were analysed with the RTCA software and expressed as the Normalized Cell Index at the time of the treatment with PPA, an arbitrary unit corresponding to the number of cells present per well.

The results obtained, and shown in FIG. 1, demonstrate that up to 5 μg/ml of PPA, no cellular toxicity is observed, highlighted with higher doses of inhibitor (25-50 μg/mL) and represented by the curves placed below the control curve, corresponding to the cells in the presence of only the culture medium, obtained with the control. It should be noted that said concentration (5 μg/ml) is markedly higher than the biologically active PPA concentrations, whose normal range of use was 10-100 ng/ml.

Example 2. PPA is Able to Inhibit the Expression of SerpinB3 Both Induced by Exogenous SerpinB3 and its Endogenous Constitutive Expression For the experiments to inhibit the exogenous induction of SerpinB3, the monocytic THP-1 line that does not express SerpinB3 or the cell line derived from HT29 colon tumor that expresses low levels of SerpinB3 was used. PPA was added in culture at a concentration of 1-100 ng/ml alone or in combination with recombinant SerpinB3 (SB3) at a concentration of 20-200 ng/ml to the cells, while only culture medium was added to the control wells. After 24 hours of treatment, the cells were collected by scraper and the extraction of total cell RNA and reverse transcription were performed according to standard protocols. SerpinB3 mRNA levels were measured by real-time PCR (sense: 5'-AACTCCTGGGTGGAAAGTCAA-3' (SEQ ID NO:1); reverse 5'-ACCAATGTGGTATTGCTGCCAA-3' (SEQ ID NO:2)).

For the inhibition of the expression of endogenous constitutive SerpinB3, tumor cells expressing constitutively SerpinB3 deriving from oesophagus (OE33) and liver tumor cells HepG2 transfected to stably express SerpinB3 (HepG2/SB3) and that in previous experiments had demonstrated significantly higher proliferative activity and cell invasiveness than the SerpinB3 non-expressing esophagus lines or HepG2 transfected with only the empty plasmid were used. They were seeded in 6-well plates and kept for 24 hours before treatment, each in its own complete culture medium in (Sigma-Aldrich, Milan, Italy). PPA (1'-piperidin propionic acid) was then added at a concentration of 10-100 ng/ml in PBS.

As the data in FIG. 2 demonstrate, the expression of SerpinB3 was found to be markedly increased by the treatment with exogenous SerpinB3 (in particular in THP-1 cells) and the addition of PPA reduces in a dose-dependent manner both its expression induced by exogenous treatment and its constitutive one. It should be noted that concentrations of 1-10 ng/ml are already able to reduce the synthesis of SerpinB3 by about 50%.

Example 3. PPA Reduces Cell Proliferation Induced by Serpinb3

Figure 3:
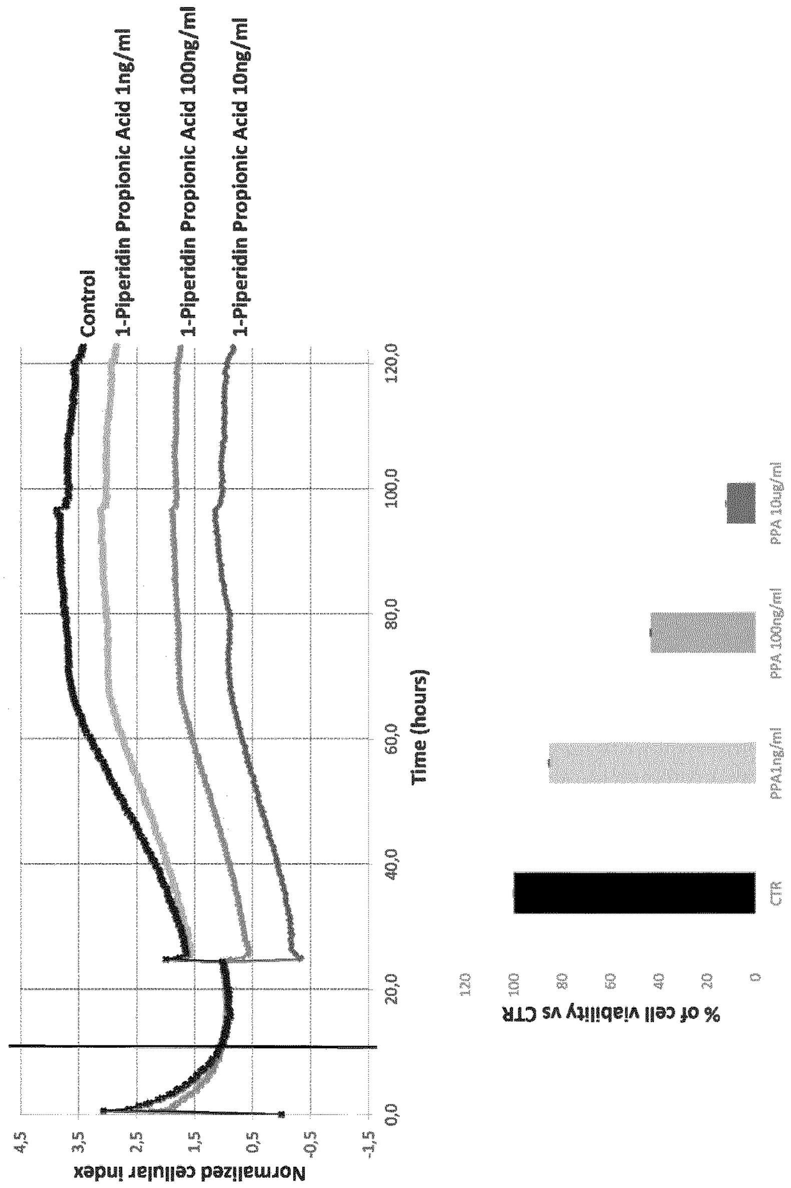
FIG. 3. Cell proliferation curves on THP-1 cells of monocytic origin stimulated with exogenous SerpinB3 (control) in the presence of PPA (FIG. 3 A) and processed as Normalized Cellular Index (FIG. 3B). The addition of PPA to monocytic cells (THP-1) stimulated with exogenous SerpinB3 not only reduces the expression of SerpinB3, but also their proliferative activity in a dose-dependent manner, as described in Example 3.

To evaluate cell proliferation in real time, the xCELLigence instrument (ACEA Biosciences, Inc., San Diego, CA, USA) was used, as described in Example 1. THP-1 cells of monocytic origin were used, whose incubation with exogenous recombinant SerpinB3 (20 ng/ml) had induced a marked increase in the synthesis of endogenous SerpinB3, as reported in Example 2. A suspension of $4\times10^4$ cells in quadruplicate was seeded in each well of an E-16 plate, cultured in complete RPMI medium (Sigma-Aldrich, Milan, Italy). The cells incubated with SerpinB3 alone or in the presence of PPA (1 ng/ml-10 ng/ml-10 μg/ml) were monitored for up to 120 hours by the xCELLigence instrument and the cell proliferation curves shown in FIG. 3 were processed and expressed by the RTCA software as the Normalized Cell Index.

The addition of PPA not only reduces the expression of SerpinB3, but a contextual reduction of the proliferative activity which has proved to be dose-dependent is documented.

Example 4: PPA Inhibits the Expression of Cytokines Induced by SerpinB3 that Reduce Immunosurveillance It has been documented that SerpinB3, in addition to inducing resistance to cell death and increased proliferation, is able to induce a reduction in tumor immunosurveillance, in particular through the increased production of cytokines such as CCL15, recently involved in the reduction of immune surveillance in hepatocellular carcinoma, and the immune checkpoint molecule PD-L1, towards which several new antitumor drugs are directed.

Figure 4:
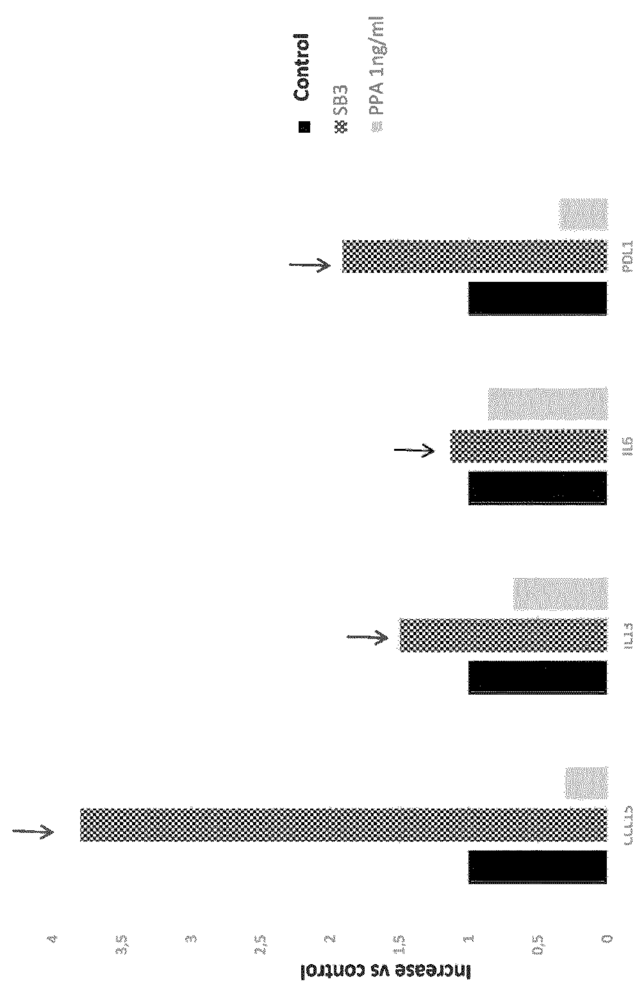
FIG. 4. Experiments on THP-1 cells of monocytic origin after stimulation with exogenous SerpinB3. The results obtained document that THP-1 monocytic cells, after stimulation with exogenous SerpinB3, which is present in the tumor microenvironment, produce high levels of cytokines, especially CCL15 and PD-L1 and that these are markedly reduced by the PPA even at very low doses (1 ng/ml). As described in Example 4, these data highlight how PPA is able to restore immune control through the suppression of SerpinB3-induced immune depression.

The results obtained shown in FIG. 4 document that THP-1 cells of monocytic origin, after stimulation with exogenous SerpinB3, which can be present in the tumor microenvironment, produce high levels of cytokines, especially CCL15 and PD-L1 and that these are markedly reduced by the PPA at very low doses (1 ng/ml). These data document how PPA is able to restore immune control through the suppression of immune depression induced by SerpinB3.

Example 5: PPA Induces Restoration of Sensitivity to Chemotherapeutic Drugs

Figure 5:
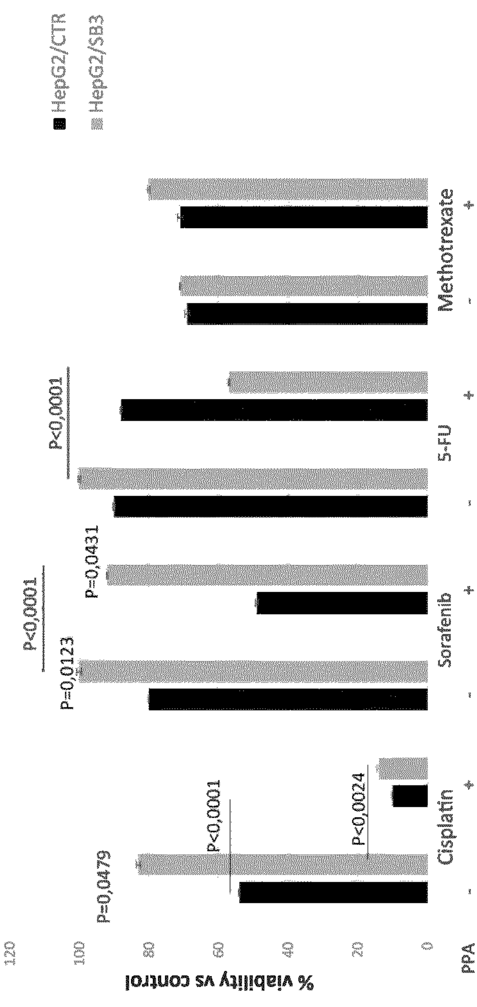
FIG. 5. The graph shows the data of cell viability experiments measured by MTT assay in HepG2 cells. The results obtained and described in Example 5 confirm that the presence of SerpinB3 confers greater resistance to cell death induced by Cisplatin and Sorafenib, while sensitivity to 5-Fluorouracil (5-FU) and Methotrexate was not different in the two cell lines. The addition of PPA resulted in a significant reduction of viability in cells with high levels of SerpinB3, treated with Cisplatin, Sorafenib and 5-Fluorouracil, while it did not change in the treatment with Methotrexate.

The SerpinB3 molecule is known to induce resistance to chemotherapy treatment. In order to evaluate whether the inhibition of said molecule is able to increase the therapeutic efficacy of antitumor drugs, HepG2 cells stably transfected to overexpress SerpinB3 (HepG2/SB3) and HepG2 cells transfected with only the empty plasmid (HepG2/CTR) have been incubated with several antitumor drugs at a concentration of 10 μM (Cisplatin, Sorafenib, 5-Fluorouracil, Methotrexate) in the absence or presence of PPA. As can be seen from FIG. 5, cell viability was measured by MTT assay. The results are expressed as a percentage of viability compared to cells incubated with only medium (CTR).

The results obtained confirmed that the presence of SerpinB3 confers greater resistance to cell death induced by Cisplatin and Sorafenib, while sensitivity to 5-Fluorouracil and Methotrexate was not different in the two cell lines. The addition of PPA resulted in a significant reduction of viability in cells with high levels of SerpinB3, treated with Cisplatin, Sorafenib and 5-Fluorouracil, while it did not change in the treatment with Methotrexate.

Example 6: PPA Reduces Multiple Resistance Profiles to Chemotherapeutic Drugs In order to understand more fully whether the resistance to chemotherapeutic drugs induced by SerpinB3 is exclusively linked to the increased resistance to cell death following the reduced activation of the mitochondrial proapoptotic cascade, the genes involved in multiple resistance to chemotherapeutic drugs have been analysed (multidrug resistance, MDR). In particular, HepG2/SB3 and HepG2 control cells (HepG2/empty) were collected after 24 hours of treatment with PPA at the doses of 10 ng/ml and 100 ng/ml and the gene expression was analysed as follows: MDR 1, MDR 2, MRP1, MRP2, MRP3, GSTP1 by real time PCR according to standard protocols.

Figure 6:
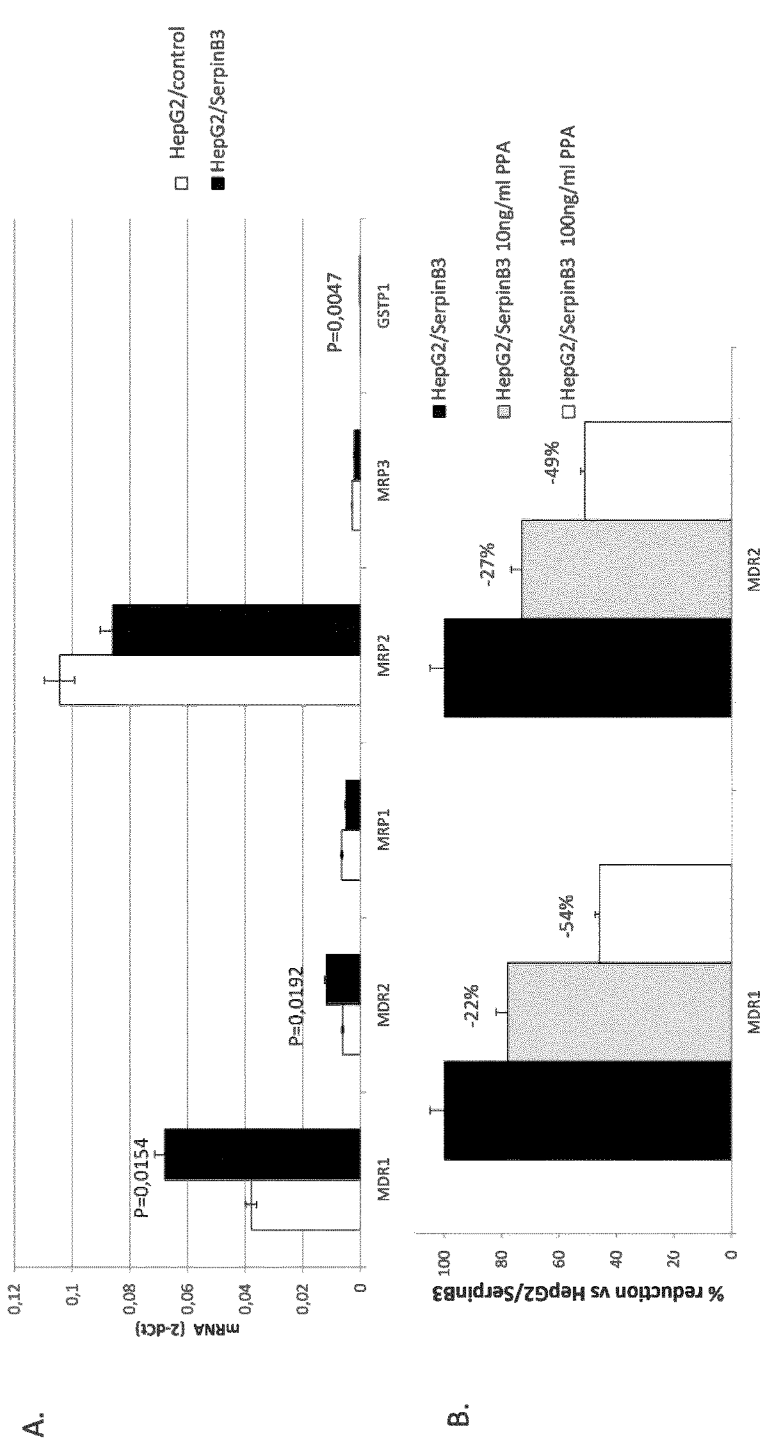
FIG. 6. Gene expression data of genes involved in the multidrug resistance in HepG2 cells are reported (FIG. 6 A). The results obtained and described in Example 6 document that the presence of SerpinB3 causes an increase in two genes involved in the resistance to chemotherapeutic drugs, in particular MDR1 and MDR2 and the treatment with PPA causes a reduction of their expression in a dose-dependent manner (FIG. 6 B). These results support the hypothesis that also the induction of MDR genes contributes to the drug resistance caused by SerpinB3, the expression of which genes is markedly reduced by PPA.

The results obtained and shown in FIG. 6 document that the presence of SerpinB3 leads to an increase in two genes involved in the resistance to chemotherapeutic drugs, in particular MDR1 and MRD2 and the treatment with PPA leads to a reduction of their expression in a dose-dependent manner. These results support the hypothesis that also the induction of MDR genes contributes to the drug resistance caused by SerpinB3, the expression of which genes is markedly reduced by PPA.

Example 7: PPA has a Protective Role in Tumor Development

To better assess the role of SerpinB3 in carcinogenesis, a mouse model of obesity-associated carcinogenesis that requires a single administration of diethyl-nitrosamine (DEN) has been developed in mice with different expression of SerpinB3. The study has been performed in mice transgenic for human SerpinB3 (SerpinB3/TG) (the initial colony was kindly provided by Prof. Cassani, Tecnogen, Caserta, Italy) and in SerpinB3 knockout mice (SerpinB3/KO) (the initial colony was kindly provided by Dr. Gary Silverman and Dr. Cliff J. Luke, University of Pittsburg, Children's Hospital, Pittsburg, PA). Moreover wild type mice of similar age were used as controls. All animals were bred and maintained with free access to pellet food and water at the Animal Care Facility of the Experimental Surgery Division of the University of Padua.

Mice were injected with (DEN, 25 mg/kg i.p.) at the age of 2 weeks. These mice were fed at the age of 6 weeks with a choline-deficient L-amino acid-defined (CDAA) diet and part of them were sacrificed after 30 months, while the remaining mice were sacrificed after 34 month. Two groups of control mice were also treated or not with PPA (weekely intraperitoneal injection of 50 ng/g of body weight) during CDAA diet. The experimental protocol was approved by the local Ethical Committee and by the Italian Ministry of Health (Authorization N. 442/2018-PR).

Figure 7:
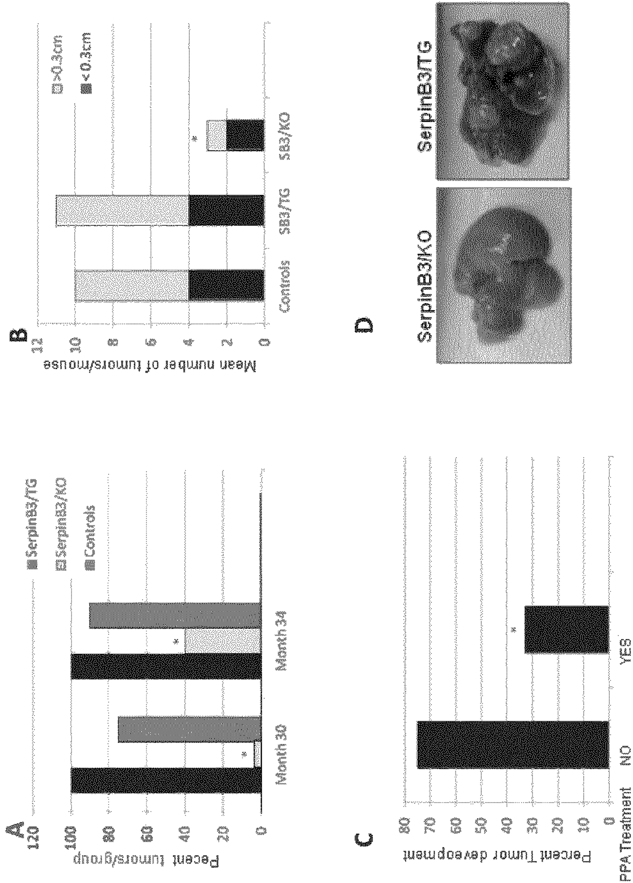
FIG. 7. Tumor nodules in experimental carcinogenesis in different groups of mice. A) Percent of tumors detected after diethyl-nitrosamine (DEN) injection followed by 30 months of choline-deficient L-amino acid-defined (CDAA) diet in the group of mice transgenic for SerpinB3 (SerpinB3/TG), in the group of mice knockout for SerpinB3 (SerpinB3/KO) and in controls. B) Mean number of tumors/mouse in SerpinB3 transgenic (SB3/TG), in SerpinB3 knockout (SB3/KO) and in control mice (Controls). Black bars represent the mean number of small tumors with a diameter<0.3 cm, while grey bars represent the mean number of intermediate/big tumors with diameter>0.3 cm. C) Percent tumor development in the liver of control mice treated or not with PPA. D) Example of livers explanted from a SerpinB3/KO mouse and from a SerpinB3/TG mouse.

Preliminary results indicate that tumor formation was found to be remarkably related to the presence of SerpinB3. Indeed, at month 30, 100% of SepinB3/TG mice and 75% of controls developed tumor nodules, while none of SerpinB3/KO mice presented detectable nodules (FIG. 7A) and the liver of these mice showed almost normal features, at variance with the liver of SerpinB3/TG mice, where tumor growth was clearly detectable (FIG. 7D). It is worth to note that mean tumor volume was significantly higher in SerpinB3/TG mice than in controls (0.7 cm vs 0.4 cm, $p<0.05$). At month 34, figures showed similar profile, with a 40% of SerpinB3/KO presenting tumor occurrence, although the mean number of tumors/mouse was smaller and mainly represented by small tumors, with a diameter<0.3 cm (FIG. 7B). Control mice treated with PPA showed a remarkable reduction of tumor formation compared with mice that did not receive the compound, supporting the protective role of PPA in tumor development through the inhibition of SerpinB3 synthesis.

From the detailed description and from the Examples reported above, the advantages achieved by the use of 1-Piperidinpropionic acid according to the present invention are evident.

The invention claimed is:

1. A method for treating a chemoresistant tumor expressing SerpinB3, said method comprising treating said chemoresistant tumor with between 1-100 ng/ml of 1-Piperidinpropionic acid (PPA) or salts thereof, wherein said chemoresistant tumor is resistant to 10 μM of a chemotherapeutic drug selected from the group consisting of cisplatin, sorafenib, 5-fluorouracil or wherein said chemoresistant tumor is resistant to immune system surveillance, and wherein said tumor is selected from the group consisting of a liver tumor and glioblastoma.

2. The method according to claim 1, wherein said tumor is a primary or secondary tumor.

3. The method according to claim 1, wherein the cells of said tumor hyperexpress SerpinB3.

4. The method according to claim 1, wherein said tumor overexpresses SerpinB3.

5. The method according to claim 1, wherein said chemoresistant tumor is resistant to a chemotherapeutic drug selected from the group consisting of cisplatin, sorafenib, 5-fluorouracil and immune system surveillance is recovered in said tumors expressing SerpinB3.

* * * * *